(12) United States Patent
Awakowicz et al.

(10) Patent No.: US 6,627,163 B1
(45) Date of Patent: Sep. 30, 2003

(54) PROCESS FOR STERILIZING CONTAINERS

(75) Inventors: Peter Awakowicz, Munich (DE); Robert Frost, Landshut (DE)

(73) Assignee: Ruediger Haaga GmbH, Altoberndorf (DE)

( * ) Notice: Subject to any disclaimer, the term of this patent is extended or adjusted under 35 U.S.C. 154(b) by 0 days.

(21) Appl. No.: 09/251,443

(22) Filed: Feb. 17, 1999

(30) Foreign Application Priority Data

Feb. 17, 1998 (DE) .......................................... 198 06 516

(51) Int. Cl.[7] .............................. A61L 2/14; F26B 3/347
(52) U.S. Cl. ....................... 422/186.23; 422/21; 422/22; 34/263; 34/265; 34/90
(58) Field of Search ............................. 422/21, 22, 26, 422/28, 305, 306, 186.23; 34/259, 263, 265, 380, 409, 417, 427, 90

(56) References Cited

U.S. PATENT DOCUMENTS

| | | | | |
|---|---|---|---|---|
| 3,753,651 A | * | 8/1973 | Boucher | 422/22 |
| 3,955,286 A | * | 5/1976 | Anrep | 34/1 |
| 4,207,286 A | | 6/1980 | Boucher | 422/21 |
| 4,507,539 A | * | 3/1985 | Sando et al. | 219/121.59 |
| 4,818,488 A | * | 4/1989 | Jacob | 422/23 |
| 5,056,144 A | * | 10/1991 | Cornelius | 331/49 |
| 5,262,125 A | * | 11/1993 | Goodman | 422/23 |
| 5,325,020 A | * | 6/1994 | Campbell et al. | 422/21 |
| 5,904,866 A | * | 5/1999 | Kasper | 219/121.43 |
| 6,060,019 A | * | 5/2000 | Spencer et al. | 422/23 |

* cited by examiner

Primary Examiner—Elizabeth McKane
(74) Attorney, Agent, or Firm—Crowell & Moring LLP

(57) ABSTRACT

In order to sterilize previously washed containers in an evacuable reactor, a low pressure plasma is generated by a high frequency generator. A microwave generator is also and can be switched on for drying the container before the plasma is ignited.

7 Claims, 1 Drawing Sheet

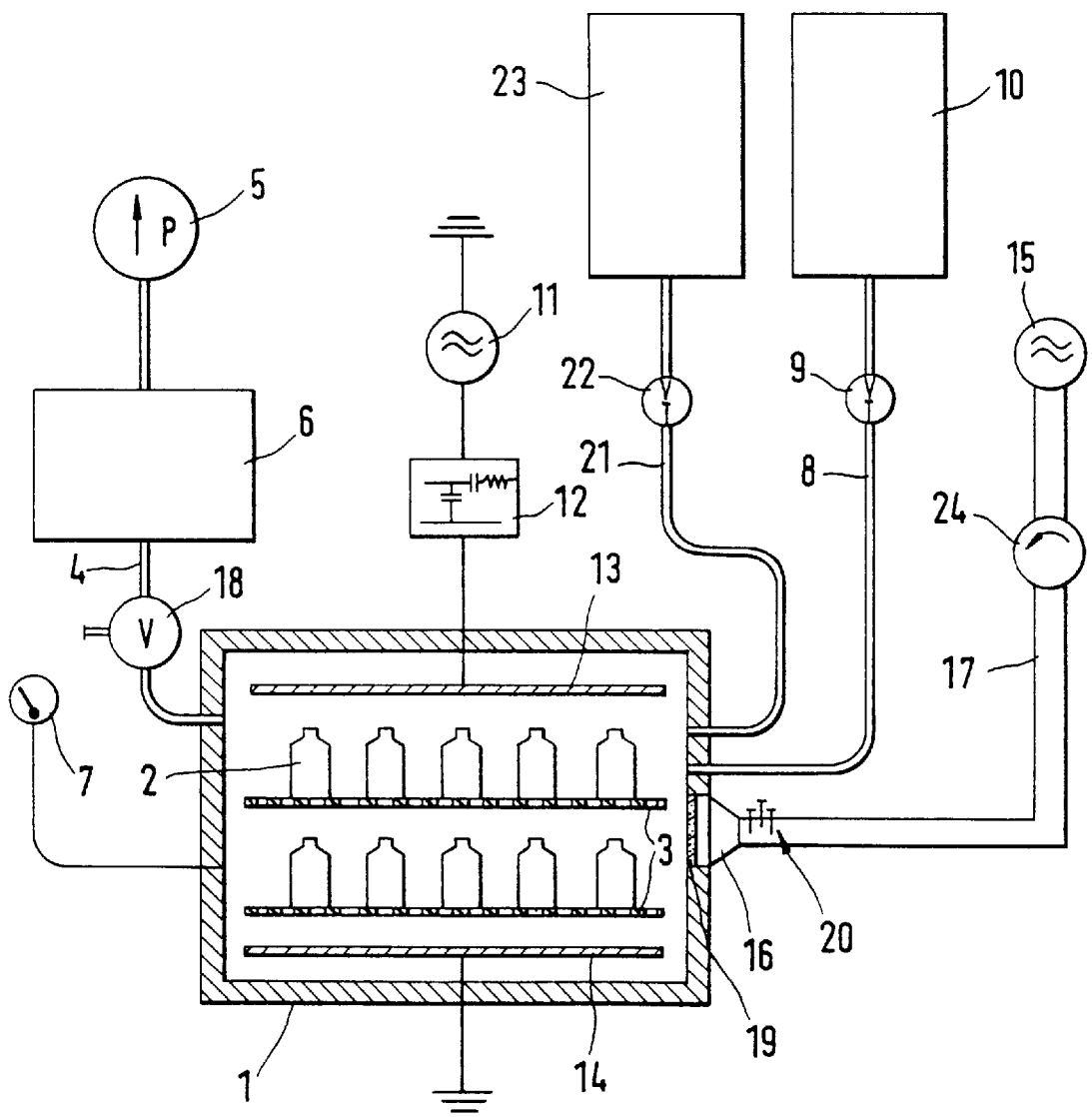

PROCESS FOR STERILIZING CONTAINERS

BACKGROUND OF THE INVENTION

This application claims the priority of German Application No. 198 06 516.7, filed Feb. 17, 1998, the disclosure of which is expressly incorporated by reference herein.

The present invention relates to a process for sterilizing containers in an evacuable reactor by way of a low pressure plasma, as well as to a device for carrying out the process.

U.S. Pat. No. 4,207,286 discloses that, in the reactor housing the containers, a low pressure is created and an alternating current plasma is sourced. The frequency sourcing can take place either in a capacitive or inductive manner via a high frequency generator or alternatively by way of a microwave generator. The containers in the reactor are already in a state which permits sterilization by the low pressure plasma.

Such prerequisites are, however, not on hand in certain areas of application. In the pharmaceutical industry or in filling re-usable bottles, for example, it is necessary to clean the usually glass or plastic containers before sterilization by washing them. Before they reach the sterilizing installation, the containers go through a washing machine, after which they are still covered with small amounts of rest water. In this respect it should be noted here that in standard thermal or wet-chemical aseptics, the rest water presents no problem, as the containers are again wetted with process fluids, or in the case of thermal sterilization, where the rest water evaporates anyway during the process.

Rest water, however, as well as other layers found on the container surfaces, hinder the process of sterilization by a low pressure plasma. The plasma then cannot reach the surfaces to be sterilized nor the germs contained in the fluids.

When the reactor is evacuated to the pressure level required for sterilization, the boiling point of the water drops to such a degree as the pressure is reduced such that the rest water, starting at the surface, subsequently starts to evaporate already at room temperature. The energy required for this is taken predominantly from the lower lying fluid layers, which can then freeze over. The resulting layer then present on the container surfaces renders plasma sterilization impossible.

An object of the present invention is to use a low pressure plasma in a reactor to sterilize containers which have been previously washed and which subsequently have rest water amounts on their surfaces.

This object has been achieved in accordance with the present invention in that the containers in the reactor are first of all dried by microwaves and that the plasma is ignited only after the drying process is completed. The drying process can occur at atmospheric pressure, but also completely in a vacuum.

In contrast to the above mentioned prior art, the microwaves in the case of the present invention do not serve the actual process of sterilization, but rather the preparation of the containers for the sterilizing process, namely the removal of rest water amounts. Thereby, the surfaces of the containers are put into a state whereby they can be subsequently sterilized by a low pressure plasma at a low temperature. Drying off of the rest water amounts by microwaves can be carried out speedily without the containers heating up greatly, so that a cooling down in preparation for a possible filling process is not necessary.

The ice layer formed from rest water during evacuation of the reactor absorbs the microwave energy and becomes warm. The pressure in the reactor, and thus the boiling point of the liquid, can be selected at such a low level that, at the point of liquification, the ice may already evaporate, that is, sublime. As in particular in a sublimation process, no liquid and thus no heatable water is present on the surface of the containers, the containers cannot therefore be heated up by the microwaves. In addition, the evaporating liquid continuously withdraws the thermal energy from the lower lying ice layers and thus cools the same. After all water and ice has been removed, almost no more microwave energy is absorbed in the reactor, so that the microwave energy density increases, as at first, the microwaves are still beamed in. The pressure in the reactor also rapidly drops significantly due to the absence of water vapor, insofar as during the process, the suction action remains constant.

Both these aspects, namely dropping pressure and increasing energy density, can be utilized for controlling the ignition of the plasma necessary for actual sterilization. It would appear most purposeful to determine the end of the drying process by monitoring the pressure, that is by measuring the absolute values of the pressure and/or by measuring the time dependance of the pressure course. Here care should be taken that during or after the end of the drying process, it does not come to a premature, undesired ignition of a microwave plasma due to the increasing energy density. The microwave plasma may locally ignite and thus may result in local overheating and possibly in damage to the containers or the reactor components.

In order to generate and maintain the plasma required for sterilization, a high frequency generator is switched on and the microwave generator is switched off at the latest after the plasma has been ignited. High frequency generators, whose frequency can be either capacitively or inductively sourced, function, for example, at a permitted frequency of 13.56 MHz. Containers can be sterilized using an alternating current plasma generated in this way. The microwave generator, not needed while the plasma is maintained, and which may be switched off before the plasma is ignited, operates in contrast at a higher frequency, for example, at a permitted frequency of 2.45 Ghz.

For supporting plasma ignition, the present invention switches off the microwave generator only after the high frequency generator has been switched on. This is particularly helpful in the case of relatively large and high reactors, when the high frequency generator cannot generate sufficient field strength for the ignition. In this case, a momentary, local break-through generated by microwaves can significantly facilitate the ignition of the sterilization plasma. A high frequency generator can be more economically designed when it does not have to supply the ignition field strength, which is significantly higher than that required to maintain a discharge. Large reactors according to the present invention occur than, for example, when the evacuable space amounts to more than 0.1 $m^3$ or when the height of the reactor is higher than around 10 cm.

In order to source the necessary microwave power in the reactor during the drying process, the impedance of the charged reactor must be adapted to match the characteristic wave impedance of the microwave generator and the waveguide. For this purpose, an impedance converter, for example a triple screw transformer, is provided, which is applied in close proximity to the reactor. As the reactor impedance can alter very quickly due to the decreasing amount of water or ice during the drying process, a temporary mismatch cannot be avoided. This effects the reflection of a more or less large part of the power delivered by the microwave generator back to the microwave generator which usually takes the form of a magnetron. In order to protect the microwave generator, a so-called circulator or the like which is mounted between the impedance converter and the microwave generator and deflects the reflected wave into, for example, a water resistor.

In a further embodiment of the present invention, a vacuum buffer is provided between the reactor and the vacuum pump in order to accelerate the evacuation of the reactor.

BRIEF DESCRIPTION OF THE DRAWINGS

These and further objects, features and advantages of the present invention will become more readily apparent from the following detailed description which refers to an accompanying sole FIGURE which is a schematic, partial cross-sectional view of an embodiment of the reactor sterilization system for carrying out the process.

DETAILED DESCRIPTION OF THE DRAWING

The reactor 1 serves to dry and sterilize previously washed containers. Preferably perforated transport belts 3 transport a plurality of containers 2 through sealable entry and exits openings (not shown) to the reactor 1 and transport them away therefrom. The containers 2 are preferably made of glass or plastic, for example PET, and are not electrically conductive.

The reactor 1 is connected by vacuum conduit 4 to a vacuum pump 5 which can generate a vacuum up to approximately 0.1 Pa in the reactor 1. A vacuum buffer 6 can be inserted between the reactor 1 and the vacuum pump 5 to permit an accelerated evacuation of the reactor 1. The vacuum buffer 6 can then be pumped when the reactor 1 is separated off from the continuously running vacuum pump 5 by an isolating valve 18. A pressure gauge 7 is connected to the reactor 1, with which pressure gauge 7 the absolute value of the pressure and/or the temporal or time-related course of the pressure can be measured.

Gas to be ionized can be fed into the evacuable reactor 1 by a supply pipe 8. Hydrogen or helium are suitable gases because they both have a high ionization energy. A gas can also be applied which supports the sterilization process by the formation of radicals, for example at places which are not easily accessible by the plasma. The flow of gas is regulated by a choker valve 9. A gas storage container 10 is provided for the gas.

A high frequency generator 11 of, for example, 13.56 MHz or another permitted frequency, serves to ignite the low pressure plasma necessary for the actual sterilization. The high frequency generator 11 generates an alternating voltage, which is transferred to the plasma to be formed by a so-called "matchbox" 12. The matchbox 12 serves to balance the impedance of the load resistance on the characteristic wave impedance of the high frequency generator 11. Inside the reactor there are two electrodes 13, 14, of which the electrode 13 is connected to the alternating voltage and the electrode 14 is grounded.

A microwave generator 15 serves to remove rest water before actual sterilization begins and operates at, for example, 2.45 GHz or another permitted frequency. The microwaves are, in this case, beamed in by a wave guide 17. In the area of the reactor 1, the wave guide 17, which has a rectangular cross section, is expanded to form an antenna 16 which terminates in the direction towards the reactor 1 in, for example, a quartz glass, microwave-transparent window 19. The window 19 must be mechanically very stable because a vacuum prevails in the reactor 1, while atmospheric pressure prevails in the antenna 16 and the wave guide 17.

When the microwave is beamed into the reactor 1, stationary waves can arise. This results in spots where the field strength and thus the power yield reaches a maximum value, but also in spots where the power yield is practically nil. A so-called scrambler (not shown) can therefore be arranged in relation to the antenna 16 inside or outside the window 19. The scrambler ensures a continually changing irradiation rate, and thus ensures that all places in the reactor 1, at least for periodically recurring timespans, are supplied with field strength and thus with microwave energy.

In order to match the impedance of the charged reactor 1 to the characteristic wave impedance of the wave guide 17, an impedance converter 20 is provided such as, for example a known triple-screw transformer. For the protection of the microwave generator 15 in the event of a mismatch, a circulator 24 is applied between the impedance converter 20 and the microwave generator 15 and branches off the reflected wave into a water resistor for example, i.e., in a water-cooled resistor, which has the same characteristic wave impedance as the wave guide 17.

Before or during the evacuation of the reactor 1, the microwave generator 15 is switched on. The generator 15 does not play a role in generating and maintaining a plasma but rather removes the remaining water or the ice resulting from the rest water by a drying process. Only after the drying process is completed is the plasma ignited by the high frequency generator 11. Ignition can still be supported by the microwave generator 15 before the latter is switched off. The plasma maintained by the high frequency generator 11 provides the actual sterilization of the containers 2.

It can be purposeful in certain circumstances to use a separate drying process gas which is not easily transformed into the plasma state. That is, the drying gas has as high a break-through field strength in the relevant pressure area as possible to prevent an undesired ignition of the microwave plasma. If desired, an additional gas container 23 can be provided, out of which a separate drying process gas is fed to the reactor 1 by a supply pipe 21 and a choker valve 22.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An arrangement for low pressure plasma sterilizing at least one re-usable container covered with rest water resulting from a preceding washing process, comprising
   a plasma reactor configured for microwave drying the at least one container in a vacuum created by a vacuum pump, and
   a high frequency generator configured to be switched to a state for generating and maintaining low-pressure plasma used for sterilization only after the drying is completed wherein the microwave drying is switched off at a time no later than ignition of the plasma such that sterilization effectively occurs using the low pressure plasma without formation of an ice layer from the rest water during evacuation of the reactor, and wherein a vacuum buffer is provided to accelerate evacuation between the reactor and the vacuum pump.

2. An arrangement according to claim 1, wherein a separate gas supply system is provided for the drying process.

3. An arrangement according to claim 1, wherein, in order to protect the microwave generator, a device for preventing excessive microwave reflection is operatively arranged in relation to the microwave generator.

4. An arrangement for low pressure plasma sterilizing at least one re-usable container covered with rest water resulting from a preceding washing process, comprising
- a plasma reactor configured for microwave drying the at least one container in a vacuum, and
- a high frequency generator configured to be switched to a state for generating and maintaining low-pressure plasma used for sterilization only after the drying is completed wherein the microwave drying is switched off at a time no later than ignition of the plasma such that sterilization effectively occurs using the low pressure plasma without formation of an ice layer from the rest water during evacuation of the reactor, and wherein an impedance converter is provided to match the impedance of the charged reactor to the characteristic wave impedance of the microwave generator.

5. An arrangement according to claim 4, wherein, in order to protect the microwave generator, a device for preventing excessive microwave reflection is operatively arranged in relation to the microwave generator.

6. An arrangement according to claim 5, wherein a vacuum buffer is provided to accelerate evacuation between the reactor and a vacuum pump.

7. An arrangement according to claim 6, wherein a separate gas supply system is provided for the drying process.

* * * * *